United States Patent [19]
Farley et al.

[11] Patent Number: 5,372,588
[45] Date of Patent: Dec. 13, 1994

[54] TROCAR HAVING BLUNT TIP

[76] Inventors: Kevin Farley, 4227 Susan Dr., Williamsville, N.Y. 14221; Daniel M. Gudeman, 526 Chesterfield La., Barrington, Ill. 60010

[21] Appl. No.: 981,173

[22] Filed: Nov. 24, 1992

[51] Int. Cl.[5] ............................................. A61M 5/178
[52] U.S. Cl. ...................................... 604/164; 604/170; 604/239; 604/264; 606/167; 606/181; 606/183; 606/185
[58] Field of Search ................ 128/751, 753; 273/416, 273/419, 420; 30/151, 152, 162, 366, 367, 368; 604/158, 160, 161, 162, 164, 165, 166, 170, 239, 263, 264, 272, 274, 283, 273; 606/159, 167, 170, 172, 181, 182, 183, 184, 185

[56] References Cited

U.S. PATENT DOCUMENTS

| | | |
|---|---|---|
| 769,829 | 9/1904 | Mott . |
| 3,036,396 | 5/1962 | Swails ................... 273/419 |
| 3,168,313 | 2/1965 | Lint ....................... 273/419 |
| 4,243,048 | 1/1981 | Griffin . |
| 4,517,965 | 5/1985 | Ellison . |
| 4,601,710 | 7/1986 | Moll ...................... 604/274 |
| 4,617,929 | 10/1986 | Gill . |
| 4,997,419 | 3/1991 | Lakatos et al. ......... 606/190 |
| 5,029,573 | 7/1991 | Chow . |
| 5,078,407 | 1/1992 | Carlston et al. ........ 273/421 |
| 5,112,063 | 5/1992 | Puckett ................. 273/416 |
| 5,116,353 | 5/1992 | Green . |
| 5,133,725 | 7/1992 | Quadri . |
| 5,137,282 | 8/1992 | Segar et al. ........... 273/421 |

Primary Examiner—John D. Yasko
Assistant Examiner—N. Kent Gring
Attorney, Agent, or Firm—William J. Crossetta

[57] ABSTRACT

A trocar has an elongated body with a frustro-conical end which terminates in a blunt tip. A plurality of blades are radially attached to a blade housing connected to the trocar body. In one embodiment the blade housing moves toward the trocar body in response to a force causing the blades to extend to a cutting position. When the force is removed the blades return to a retracted position.

20 Claims, 3 Drawing Sheets

TROCAR HAVING BLUNT TIP

FIELD OF THE INVENTION

This invention relates to a surgical trocar and more particularly to a trocar having a dialating and tapered blunt tip to minimize the likelihood of inadvertent injury to viscera and other internal tissue.

DESCRIPTION OF THE PRIOR ART

Trocars are surgical instruments used to make a hole into a body cavity. Trocars are generally adapted to be used together with a tubular trocar sleeve or cannula. Once the body cavity has been punctured by the trocar, the trocar is removed from the cannula, thereby leaving the cannula extending into the body cavity. This cannula can then be used to insert endoscopic or other surgical instruments.

In various types of abdominal surgical procedures a veress needle is inserted into the patient below the umbilicus in the mid-line. After the needle is in position it is connected to an insufflation apparatus which injects a gas, typically carbon dioxide, into the abdominal cavity. After the abdominal cavity is inflated the needle is withdrawn. The needle puncture must then be enlarged to accommodate a trocar sleeve or cannula. This can be done by use of a scalpel or by use of a trocar having a sharp pointed tip.

The trocars of the prior art all have sharp pointed tips. They puncture the body by simply pushing the trocar against the skin. If too much force is applied to the trocar, it may strike internal organs or other tissue causing serious damage.

Green in U.S. Pat. No. 5,116,353 proposed to solve this problem by providing a spring loaded tubular safety shield positioned around the pointed tip. The safety shield is initially in its distal most position covering the sharp tip of the trocar. Exertion of pressure against the skin with the trocar causes the shield to be pushed rearwardly against a spring to expose the piercing tip of the trocar. The tip penetrates the skin and the underlying tissue. Once the tip has penetrated through the wall and has entered the body cavity, the spring forces the shield to automatically move back to its distal extended position. A major disadvantage of this shielded trocar is that the shield acts as an inhibitor or a drag on ease of entry through the abdominal wall. Therefore, the surgeon must in some instances exert extreme force. Should the shield not immediately return to a safety position upon entry into the cavity serious injury could result. Sometimes the surgeon may twist or turn the trocar during insertion which increases the trauma to the incision. Another problem with this device is that debris can become lodged between the shield and the trocar tip causing the shield to remain in a retracted position. The use of extreme force in combination with malfunction of the shield may cause inadvertent "inertial" deaths.

Yoon in U.S. Pat. No. 4,535,773 suggests several alternative safety trocar designs. In one embodiment shown in FIGS. 22–28 of this patent a spring loaded blunt probe is provided within the trocar shaft as with conventional veress needles. The blunt probe is adapted to reciprocally slide through an aperture in a sharp trocar tip such that when the trocar enters the body cavity the blunt probe springs distally forward through the aperture to prevent the sharp trocar tip from piercing body organs. As with the safety shielded device if the spring malfunctions the blunt probe will not move forward and the potential for serious injury exists.

There is a need for a trocar which will not cause damage to bodily tissue and organs when it inadvertently strikes them.

SUMMARY OF THE INVENTION

We provide an improved trocar which has a blunt tip. Behind the blunt tip are a plurality of radial blades. The trocar is specifically designed to enter the puncture created by the veress needle. As the blunt end penetrates that puncture, radial blades behind the blunt end extend outwardly to enlarge the puncture to permit entry of the trocar sleeve. Since the blades are behind the blunt tip, there is no sharp point which could inadvertently strike and damage human organs or tissue.

Other objects and advantages of our trocar will become apparent from a description of certain present preferred embodiments which are shown in the drawings.

DESCRIPTION OF THE PREFERRED EMBODIMENTS

Figure 1:
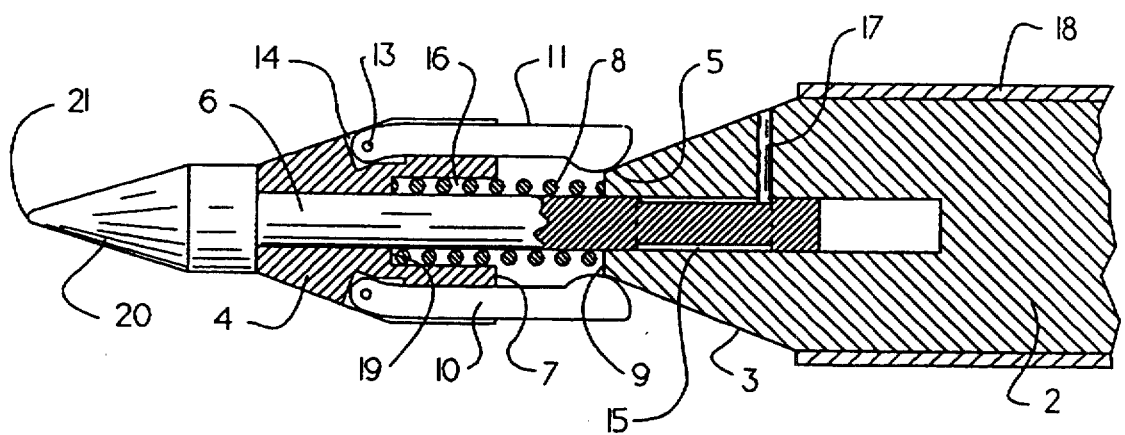
FIG. 1 is a side view partially in section of a first present preferred embodiment of our trocar extending from a cannula and having the blades in a retracted position.
Figure 2:
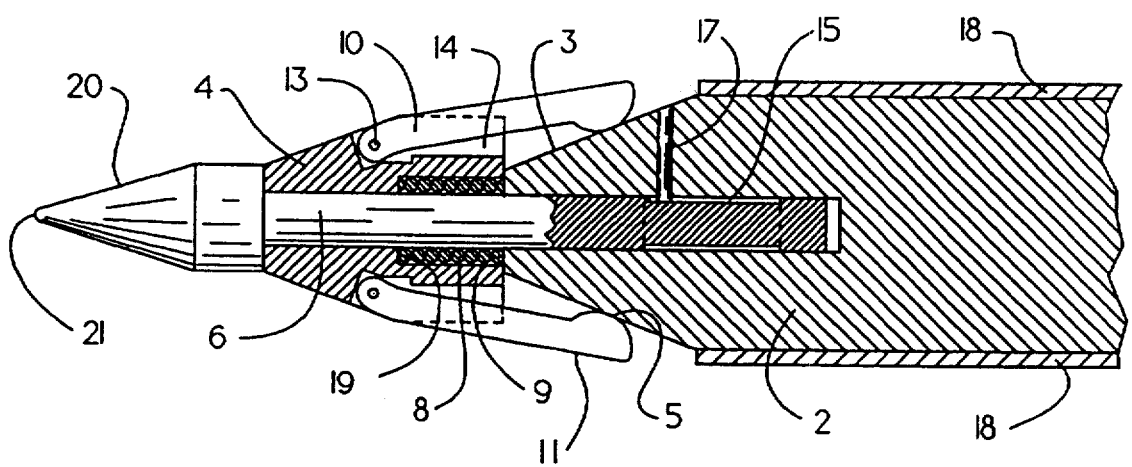
FIG. 2 is a side view partially in section of the embodiment of FIG. 1 with the blades in an extended position.
Figure 3:
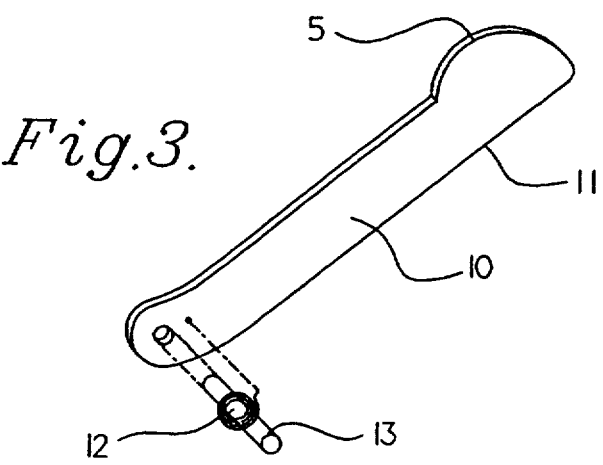
FIG. 3 is a perspective view of a blade, pin and spring used in the embodiments of FIGS. 1 and 2.

The first present preferred trocar 1 is shown in FIGS. 1, 2 and 3. This trocar consists of a tubular trocar body 2 having a tapered lower body portion 3. A blade housing 4 is connected to the tapered portion of the trocar body by connecting rod 6. A spring 8 surrounds the connecting rod 6. One end of the spring abuts the distal end 9 of the lower trocar portion. The second end of the spring abuts the inner wall 19 within the base 7 of the blade housing. Thus, a portion of the spring is within cavity 16 of the blade housing. A circumferential groove 15 is provided around connecting rod 6 to retain the rod within the trocar body 2 and allow the blade housing 4 to rotate relative to the trocar body 2. A plurality of radial blades 10 having cutting edges 11 are pivotably connected to the blade housing by blade pin 13. In the retracted position shown in FIG. 1 the blades fit within slot 14 in the blade housing. A bougie type tip 20 having a blunt distal end 21 is attached to the blade housing. We prefer that this bougie tip be screwed in to the connecting rod 6 which extends through the blade housing 4, Our trocar is particularly adapted for use in surgery where a needle puncture has been initially made. The blunt end 21 of the tip 20 is pressed through the needle puncture forcing the tip into the needle puncture. As pressure is applied the blade housing 4 will move toward the trocar body 2 compressing spring 8 as shown in FIG. 2. As the blade housing 4 moves toward the trocar body, a portion of the underside 5 of the blade 10 will engage the tapered portion 3 of the trocar body. As the blade housing continues to move toward the trocar housing, the blades 10 will ride up the tapered portion 3 causing a portion of the blades to move to an extended position shown in FIG. 2. Thus, as the trocar is forced through the skin, blades 10 will enlarge the puncture so as to permit a cannula 18 to be inserted into the body cavity. Preferably, the trocar has been inserted through the cannula 18 before the procedure begins as shown in FIGS. 1 and 2. When the blade housing enters the body cavity, spring 8 will expand causing the blade housing 4 to move away from the trocar body 2. A blade spring 12 is provided for each blade pin 13 to cause the blades to return to the retracted position, shown in FIG. 1, as the blade housing moves away from the trocar body. In the event that the trocar after passing through the skin strikes a body organ or tissue it will cause little or no damage. No damage occurs because our trocar tip 20 has a blunt end 21 which cannot pierce or tear body tissues.

Figure 4:
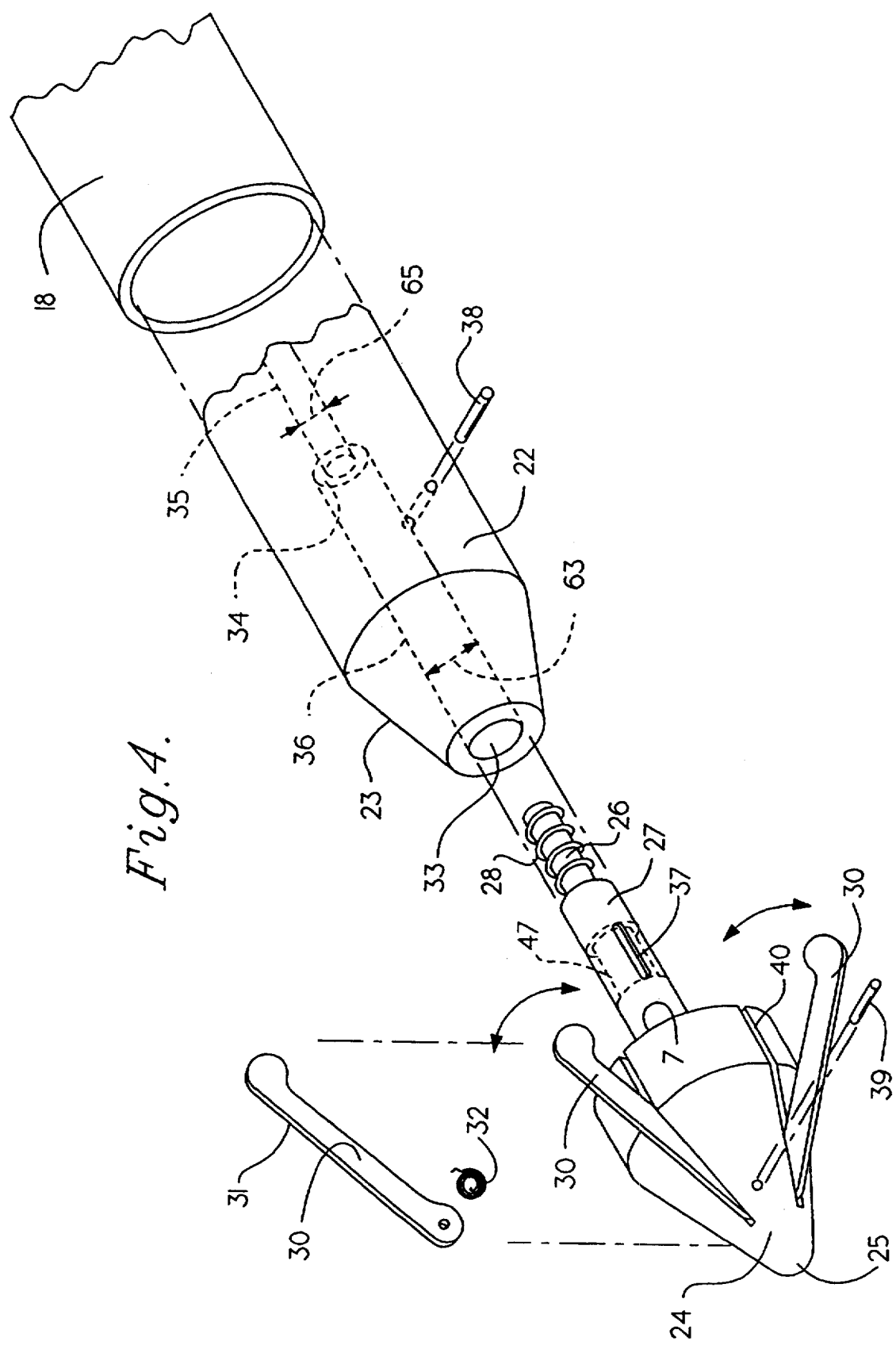
FIG. 4 is an exploded view of a second present preferred embodiment.

In FIG. 4 we show the second embodiment of a trocar which is quite similar to the embodiment of FIGS. 1 and 2. We provide a trocar body 22 which extends through the cannula or sleeve 18. The body has a tapered portion 23 and a cavity 33 which has a main chamber 36 having a major diameter 63, a shoulder 34 and neck portion 35 having a minor diameter 65. The cavity 33 may extend beyond the tapered portion 23 into the trocar body 22. Connecting rod 26 fits within the main chamber 36 and neck 35 of cavity 33. Spring 28 rests against shoulder 34. A transition rod 27 extends between connecting rod 26 and base 7 of blade housing 24. A slot 37 is provided in the transition rod 27. Retainer pin 38 extends through a hole in the body and into slot 37 in the transition rod. This arrangement permits relative longitudinal movement, but not rotation, of the blade housing 24 with respect to the tapered end 23 and trocar body 22. Alternatively, one could use a circumferential groove 47 shown in chain line in place of slot 37. The pin and groove arrangement permits both longitudinal and rotational relative movement of the blade housing 24 with respect to the trocar body 22.

A plurality of blades 30 each having a cutting edge 31 are pivotably attached to the blade housing 24 using connecting pins 39. Spring 32 is provided to bias the blades 30 into a retracted position. However, the blades can pivot to an extended position as indicated by the arrows. The embodiment of FIG. 4 operates in much the same manner as the embodiment of FIG. 1. When no force is acting on the blunt tip 25 of the blade housing it will be in an extended position so that the blades are retracted within the respective blade slots 40. In this position the trocar will look much like the trocar of FIG. 1. When the tip of the trocar is pushed against a body wall it will cause the blade housing 24 to move toward the trocar body 22. This movement will cause blades 30 to ride up the tapered portion 23 of the trocar body to an extended position. After the trocar has entered the body cavity, the insertion force will be removed allowing spring 28 to expand to its rest position and the blades to return to their respective slots.

Figure 5:
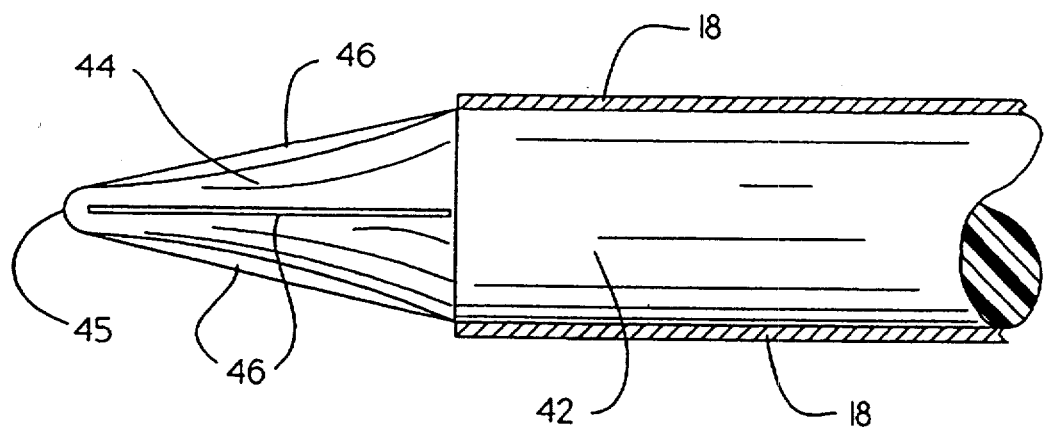
FIG. 5 is a side view of a third present preferred embodiment of our trocar.

The embodiment of FIG. 5 has an elongated trocar body 42 terminating in a blade housing 44. The blade housing may be integrally molded with the trocar body or may be removable. The blade housing terminates in a blunt end 45. A plurality of blades 46 are radially arranged around the circumference of the blade housing. The blades terminate a short distance from the blunt tip 45. As the trocar is forced against a needle puncture in the skin the blunt end will enter the needle puncture and the trocar will continue through the skin. Blades 46 will enlarge the puncture so that a cannula or sleeve 18 preferably surrounding the trocar body can be inserted.

Figure 6:
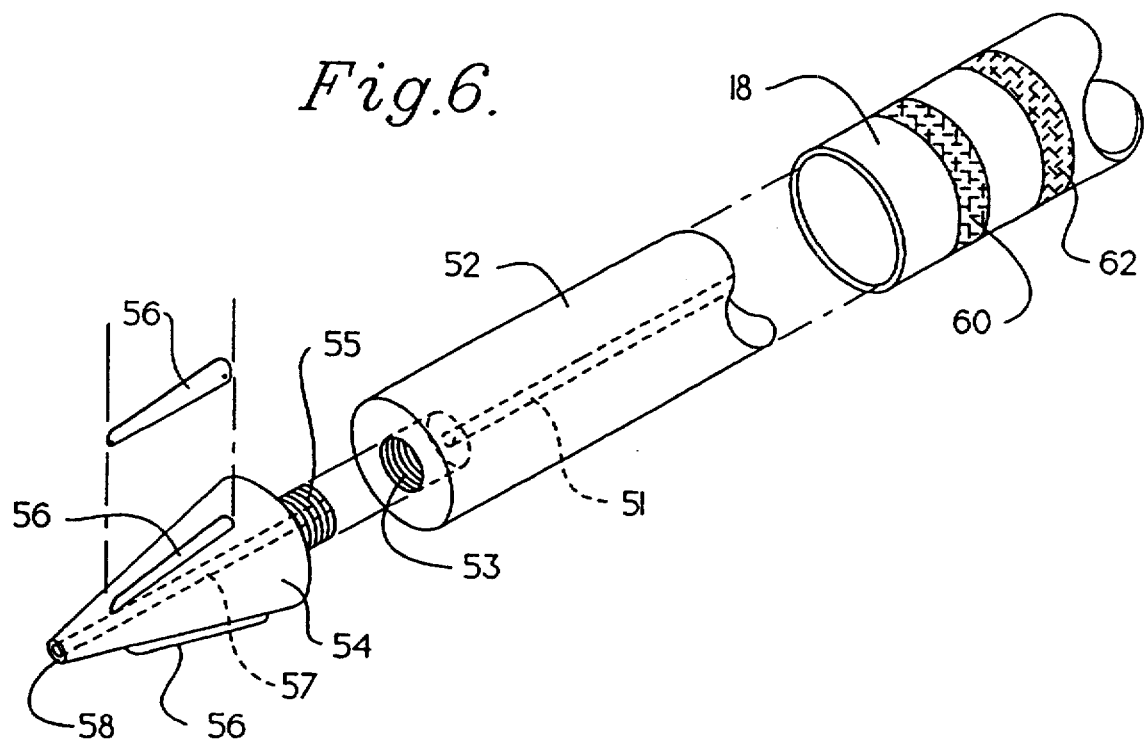
FIG. 6 is an exploded view of a fourth present preferred embodiment of our trocar.

The embodiment of FIG. 6 has an elongated trocar body 52 having a longitudinal channel 51 passing therethrough. A threaded cavity 53 is provided at the distal end of the trocar body 52. A frustro-conical blade housing 54 has a threaded post 55 at its base. The post is threaded into cavity 53 to connect the blade housing 54 to the trocar body. The blade housing 54 has a plurality of radial blades 56 affixed to its circumference behind the blade housing tip 58. A longitudinal passage 57 is provided through the blade housing 54. The passageway aligns with the longitudinal channels 51 through the trocar body 52. The longitudinal channel through both the trocar body 52 and blade housing 54 is preferably three millimeters. The blade housing body is preferably made of plastic such as delrin plastic. The blades 56 can be molded into the housing or attached with a snap fit or pins. Because the blade housing is detachable from the trocar body, the blade housing may be disposable with the trocar body being reusable. We prefer to provide a series of bands 60 and 62 or other markings at selected distances along the cannula 18. These markings, such as band 60 and band 62, are at selected intervals along the cannula body and will indicate to the physician the depth of penetration made by the trocar.

Trocars are typically made in 5 millimeter or 10 millimeter diameters. Our trocar body for each of our embodiments is applicable to any diameter. The trocar body can be color coded to indicate its diameter. The blunt tip of the blade housing should be approximately two millimeter in diameter. The base of the blade housing which connects to the trocar body should be of the same diameter as the trocar body. The blade housing in the embodiments of FIGS. 5 and 6 is preferably five to seven millimeters from the blunt end to the base.

In the embodiments of FIGS. 1 and 2 we prefer that the bougie type tip have a height of five millimeters from its base to its tip and blade housing 4 and 24 have a length of approximately seven millimeters. The tapered portion 3 of the trocar body is preferably eight millimeters long.

The trocar of the present invention is particularly suited for use in abdominal surgery. The entry path for the trocar/cannula is established through prudent placement and testing of the veress needle into the uninflated abdomen. The veress needle should be calibrated so one knows the depth of insertion. Thus, notation should be made as to the depth of the properly placed veress needle prior to insufflation of the peritonium. Typically, that depth will be approximately 100 millimeters. The peritonium is then insulated with approximately three liters of carbon dioxide which distends the abdomen allowing an additional working space of around 40 to 50 millimeters or about two inches. During insufflation, the abdominal wall is stretched and thus will decrease in thickness. After the veress needle is removed our trocar is placed into the pathway created by the veress needle typically having an outside diameter of 2.5 millimeters. The surgeon presses the trocar and cannula into the veress needle puncture causing the tip of the trocar to enter the pathway. If the embodiments of FIGS. 1, 2 or 4 are being used, the resistance provided by the abdominal wall will force the blade housing against the tapered portion of the trocar housing causing the blades to extend to a cutting position. In the embodiments of FIGS. 5 and 6 the blades are fixed in a cutting position. As the trocar and cannula continue through the abdominal wall, the blades will cut and enlarge the puncture so that the cannula can be properly placed. Depth markings on the cannula will indicate the depth of insertion. Since a veress needle has previously been positioned in an uninflated abdomen at a depth of 100 millimeters, the trocar should be able to be safely inserted to a depth of 135 to 150 millimeters in an insufflated patient. Use of a calibrated trocar/cannula in conjunction with a calibrated veress needle allows a judicious verification of the depth of measurement to penetrate the abdominal wall after insufflation of the patient. The blunt tip prevents inadvertent puncture or tearing of abdominal structures. When the embodiments of FIG. 1 and FIG. 4 are used, one will hear an audible click of the blade housing immediately after it reaches its forward position. That click will provide a verification that the incision has been completed and blades are retracted. The physician can then check the depth markings on the cannula against the original depth indication on the veress needle in the deflated patient to confirm that the trocar and cannula are at a safe depth.

The use of auto-retractable scalpel cutting blades eliminates drag and the need for overzealous uncontrolled force to overcome the resistance of the abdominal wall as the trocar and cannula are inserted. Because the present trocar shaft can be inserted without torquing, less trauma will occur at the puncture site. Because no torquing is needed and because the blade housing can be rotated freely on the trocar body, no transverse stress will be placed on the cutting blades which may cause breakage.

Because the blade housing is removable from the trocar body, a new blade housing can be used for each patient. Hence, a new, sterile, very sharp cutting device will be available for each patient. Sharp blades make a cleaner incision and assure that there will be less postoperative pain.

Because the blade housing can be easily molded of plastic our trocar should be less expensive than other prior art devices. The trocar body and sleeve are also easy to use, maintain, clean and sterilize. The present trocar is suitable for all surgical procedures for which trocars have been used. Minimal training is required to use the trocar and present surgical procedures need not be modified to permit use of this trocar.

Although we have shown and described certain present preferred embodiments of our apparatus, it should be understood that the invention is not limited thereto, but may be variously embodied within the scope of the following claims.

I claim:

1. A trocar comprising:
   an elongated trocar body having a tapered portion at a distal end;
   a blade housing, arranged along about a longitudinal axis of said trocar body, having a base and a blunt tip, said base of said blade housing being arranged adjacent said distal end of said trocar body;
   a plurality of elongated blades arranged radially about said blade housing and having proximal and distal ends, said proximal ends being connected to said blade housing;
   means for connecting said blade housing and said trocar body in axially opposed movable alignment;
   means for urging a distal end of a blade radially outwardly by axial movement of said blade housing toward said tapered portion of said trocar body.

2. The trocar of claim 1 comprising means for urging said distal ends radially inwardly during axial movement of said blade housing away from said tapered portion of said trocar body.

3. The trocar of claim 1 wherein said trocar body comprises a longitudinal channel at its distal end along about said longitudinal axis, sized to receive said means for connecting.

4. The trocar of claim 2 comprising spring means arranged for urging a distal end of a blade radially inwardly.

5. The trocar of claim 1 wherein the blade housing is made of plastic.

6. The trocar of claim 1 comprising means arranged for urging said blade housing axially away from said distal end of said trocar body.

7. The trocar of claim 1 comprising a cannula into which the trocar body is fitted.

8. The trocar of claim 7 comprising at least one depth marking on the cannula.

9. The trocar of claim 7 wherein the cannula is color coded to indicate trocar size.

10. The trocar of claim 1 comprising:
    a first longitudinal channel, arranged within said blade housing along said longitudinal axis of said trocar body;
    a second longitudinal channel, arranged within said trocar body along said longitudinal axis of said trocar body, which is aligned with said first channel;
    a connecting rod, extending between said blade housing and said trocar body, arranged along said longitudinal axis of said trocar body and sized to be inserted into said first and second longitudinal channels;
    a spring encircling said connecting rod and fitted between said trocar body and said blade housing.

11. The trocar of claim 10 wherein said first longitudinal channel comprises an opening through said blunt tip of said blade housing and said connecting rod comprises a tip arranged to extend from said blade housing.

12. The trocar of claim 1 wherein said means for connecting comprises a circumferential groove and wherein a pin passes through a portion of said trocar body into said circumferential groove.

13. The trocar of claim 1 wherein said means for connecting comprises a transverse slot and wherein a pin passes through a portion of said trocar body into said transverse slot.

14. The trocar of claim 10 wherein said connecting rod comprises one of circumferential groove and transverse slot arranged to accept a pin passing through a portion of said trocar body.

15. The trocar of claim 1 wherein said means for connecting comprises connecting and transition rod means, and said distal end of said elongated trocar body comprises a longitudinal channel having a shoulder; said connecting rod means having a diameter sized for insertion within said longitudinal channel, said diameter being smaller than a diameter of said transition rod means; said connecting rod means comprising a spring coiled thereon having one end arranged to engage an end of said transition rod means and another end arranged to engage said shoulder.

16. The trocar of claim 1 wherein the trocar body is color coded to indicate trocar size.

17. In a trocar comprising an elongated body, sized to pass through a cannula, and a distal end comprising blades for cutting, the improvement comprising:
   said distal end comprising a blade housing having a blunt tip;
   said blade housing having a tapered surface extending longitudinally from said blunt tip, comprising a plurality of longitudinally extending, radially mounted elongated blades with cutting edges extending radially outwardly from said tapered surface and arranged set back from said blunt tip.

18. The trocar of claim 17 wherein said blade housing is removably attached to said distal end.

19. The trocar of claim 18 wherein said blade housing comprises a threaded post which mounts, by means of mating threads, in a channel at said distal end of said elongated body.

20. The trocar of claim 17 wherein said elongated body comprises a longitudinal channel, having an opening thereto through said blunt tip.

* * * * *